United States Patent
Rassoulian

(10) Patent No.: US 10,179,122 B2
(45) Date of Patent: Jan. 15, 2019

(54) USE OF MELATONIN

(76) Inventor: Darius Rassoulian, Dusseldorf (DE)

(*) Notice: Subject to any disclaimer, the term of this patent is extended or adjusted under 35 U.S.C. 154(b) by 0 days.

(21) Appl. No.: 14/344,999

(22) PCT Filed: Sep. 13, 2012

(86) PCT No.: PCT/EP2012/067933
§ 371 (c)(1),
(2), (4) Date: Nov. 17, 2014

(87) PCT Pub. No.: WO2013/037883
PCT Pub. Date: Mar. 21, 2013

(65) Prior Publication Data
US 2015/0111941 A1    Apr. 23, 2015

(30) Foreign Application Priority Data
Sep. 16, 2011 (EP) .................... 11181683

(51) Int. Cl.
*A61K 9/00* (2006.01)
*A61K 31/4045* (2006.01)

(52) U.S. Cl.
CPC .......... *A61K 31/4045* (2013.01); *A61K 9/006* (2013.01)

(58) Field of Classification Search
None
See application file for complete search history.

(56) References Cited

U.S. PATENT DOCUMENTS

| | | | |
|---|---|---|---|
| 5,879,710 A | 3/1999 | Bromet | |
| 2002/0048551 A1* | 4/2002 | Keller | A61K 9/006 424/43 |
| 2008/0167363 A1 | 7/2008 | Barlow et al. | |
| 2009/0130238 A1 | 5/2009 | Kim et al. | |
| 2010/0119601 A1* | 5/2010 | McCarty | A61K 9/0056 424/464 |
| 2014/0120172 A1* | 5/2014 | Hata | A61K 31/202 424/522 |

FOREIGN PATENT DOCUMENTS

| | | |
|---|---|---|
| CN | 1646098 A | 7/2005 |
| EP | 0867181 | 9/1998 |
| GB | 2 434 099 A | 7/2007 |
| JP | H11-049693 A | 2/1999 |
| JP | 2007-510716 A | 4/2007 |
| JP | 2007-517040 A | 6/2007 |
| JP | 2009-539969 A | 11/2009 |
| JP | 2010-523673 A | 7/2010 |
| RU | 2250778 | 4/2005 |
| RU | 2009 137472 A | 5/2011 |
| UA | 55668 | 4/2003 |
| WO | WO 03/086352 A1 | 10/2003 |
| WO | WO 2008/148015 A1 | 12/2008 |

OTHER PUBLICATIONS

Tan (J Exp Bot. Jan. 2012;63(2):577-97. Epub Oct. 20, 2011).*
Medline, http://www.nlm.nih.gov/medlineplus/ency/article/002041.htm, accessed Jun. 15, 2015.*
Yahoo, https://answers.yahoo.com/question/index?qid=20120316080930AAMNgYo.*
Sturtz (Food Chemistry 127 (2011) 1329-1334).*
Johnny (http://www.johnnyseeds.com/p-9661-marbonne.aspx, accessed Jun. 15, 2015).*
Swift (Alcohol Health Res World 22 (1998): 54-60).*
WebMD (http://www.webmd.com/first-aid/alcohol-intoxication-treatment; accessed Jun. 15, 2015).*
Mayo (http://www.mayoclinic.org/diseases-conditions/alcohol-poisoning/basics/treatment/con-20029020; accessed Jun. 15, 2015).*
Attenburrow (Psychopharmacology ( 1996) 126:179-181).*
Kunz (The Journal of Clinical Endocrinology & Metabolism 89(1):128-134).*
Philstar (http://www.philstar.com/science-and-technology/202202/melatonin-natural-anti-stress-sleep-enhancer; Apr. 10, 2003).*
Baydas et al., "Protective effects of melatonin against ethanol-induced reactive gliosis in hippocampus and cortex of young and aged rats", *Experimental Neurology*, 194 (2005) 175-181.
Baydas et al., "Comparison of the impact of melatonin on chronic ethanol-induced learning and memory impairment between young and aged rats", *Journal of Pineal Research*, 2005, 39:346-352.
Pittler et al., "Interventions for preventing or treating alcohol hangover: systematic review of randomized controlled trials", *BMJ Online First*, bjm.com, pp. 1-4.
International Search Report and Written Opinion of the International Searching Authority dated Jan. 2, 2013 in the priority application, PCT/EP2012/067933.
Wade, Nightly treatment of primary insomnia with prolonged release melatonin for 6 months: a randomized placebo controlled trial on age and endogenous melatonin as predictors of efficacy and safety, BMC Medicine 2010, 8:51, published Aug. 16, 2010.
Russian Office Action dated Sep. 26, 2016 plus English translation.
El-Sokkary et al.; Inhibitory Effect of Melatonin on Products of Lipid Peroxidation Resulting From Chronic Ethanol Administration; Alcohol & Alcoholism; vol. 34; No. 6; pp. 842-850; 1999.
Oner et al.; Effect of Exogenous Melatonin on Ethanol-induced Changes in Na(+), K(+) and Ca(2+)-ATP-ase Activities in Ray Synaptosomes; Neurochem. Res.; vol. 27; No. 12; pp. 1619-1623; 2002.
Penning et al.; The pathology of alcohol hangover; Curr. Drug Abuse Rev.; vol. 3; No. 2; pp. 68-75; 2010.
Raghavendra et al.; Possible antioxidant mechanism in melatonin reversal of aging and chronic ethanol-induced amnesia in plus-maze and passive avoidance memory tasks; Free Radio. Biol. Med.; vol. 30; No. 6; pp. 595-602; 2001.
Japanese Office Action for Japanese Patent Application No. 2014-530214, dated May 17, 2016.
Russian Office Action for Russian Patent Application No. 2014115196 dated, Jun. 10 , 2016.

(Continued)

*Primary Examiner* — Devang K Thakor
(74) *Attorney, Agent, or Firm* — Knobbe, Martens, Olson & Bear, LLP.

(57) ABSTRACT

The present invention relates to melatonin or a pharmaceutically acceptable salt thereof for use as a medicament, the use of melatonin or a pharmaceutically acceptable salt thereof for the preparation of medicament, the use of melatonin as a food supplement and a pharmaceutical unit dosage form.

16 Claims, No Drawings

(56) References Cited

OTHER PUBLICATIONS

Ylikahri, R. H., Huttunen, M. O., Eriksson, C. J. P. and Nikkilä, E. A., Metabolic Studies on the Pathogenesis of Hangover, European Journal of Clinical Investigation, 1974, 4: 93-100. doi: 10.1111/j.1365-2362.1974.tb02320.x, Helsinki, Finland.

Heidrich H., Ott H., Beach RC, Lormetazepam—a benzodiazepine derivative without hangover effect? A double-blind study with chronic insomniacs in a general practice setting, Int J Clin Pharmacol Ther Toxicol, Jan. 19, 1981, (1):11-7.

Patricia B. Burns, MPH, Rod J. Rohrich, MD, and Kevin C. Chung, MD, MS, The Levels of Evidence and their role in Evidence-Based Medicine, Plast Reconstr Surg., Jul. 2011, 128(1): 305-310.

Damaris J. Rohsenow, Ph.D., Jonathan Howland, Ph.D., M.P.H., Sara J. Minsky, M.P.H., Jacey Greece, M.P.H., Alissa Almeida, M.P.H., and Timothy A. Roehrs, Ph.D., The Acute Hangover Scale: A New Measure of Immediate Hangover Symptoms, Addict Behav., Jun. 2007, 32(6): 1314-1320, Providence, Rhode Island.

Max H Pittler, Joris C Verster, Edzard Ernst, Interventions for preventing or treating alcohol hangover: systematic review of randomised controlled trials, bmj.com, 2005, 331:1515, Utrecht, Netherlands.

Joris C. Verster, Richard Stephens, Renske Penning, Damaris Rohsenow, John McGeary, Dan Levy, Adele McKinney, Frances Finnigan, Thomas M. Piasecki, Ana Adan, G. David Batty, Lies A.L. Fliervoet, Thomas Heffernan, Jonathan Howland, Dai-Jin Kim, L. Darren Kruisselbrink, Jonathan Ling, Neil McGregor, Rene J.L. Murphy, Merel Van Nuland, Marieke Oudelaar, Andrew Parkes, Gemma Prat, Nick Reed, Wendy S. Slutske, Gordon Smith and Mark Young, The Alcohol Hangover Research Group Consensus Statement on Best Practice in Alcohol Hangover Research, BenthamScience, Apr. 2017, vol. 3 Issue:2, Utrecht, The Netherlands.

Prat, G., Adan, A. and Sánchez-Turet, M., Alcohol hangover: a critical review of explanatory factors, Hum. Psychopharmacol. Clin. Exp., 2009, 24: 259-267. doi: 10.1002/hup.1023, Barcelona, Spain.

Richard Stephens, Jonathan Ling, Thomas M. Heffernan, Nick Heather and Kate Jones, A Review of the Literature on the Cognitive Effects of Alcohol Hangover, Alcohol & Alcoholism, Jan. 31, 2008, vol. 43, No. 2, pp. 163-170, Buxton, United Kingdom.

Joris C. Verster, The Alcohol Hangover—A Puzzling Phenomenon, Alcohol & Alcoholism, Jan. 8, 2008, vol. 43, No. 2, pp. 124-126, Utrecht, The Netherlands.

Japanese Office Action for Japanese Patent Application No. 2014-530214, dated Dec. 16, 2016 (with English translation).

Roehrs, Timothy; "Sleep Physiology and Pathophysiology"; Clinical Cornerstone; vol. 2; No. 5; pp. 1-15; 2000.

Joris C. Verster et al. "The alcohol hangover research group consensus statement on best practice in alcohol hangover research." Current Drug Abuse Reviews 3.2 (2010): 116-126.

Slutske, Wendy S et al., "Development and initial validation of the Hangover Symptoms Scale: Prevalence and correlates of hangover symptoms in college students." Alcoholism: Clinical and Experimental Research 27.9 (2003): 1442-1450.

Rohsenow, DJ et al. "The role of beverage congeners in hangover and other residual effects of alcohol intoxication: a review." Current Drug Abuse Reviews 3.2 (2010): 76-79.

Joris C. Verster et al. "Treatment and prevention of alcohol hangover." Current Drug Abuse Reviews 3.2 (2010): 103-109.

WebMD, Melatonin, Side Effects & Safety available at: https://www.webmd.com/vitamins-supplements/ingredientrnono-940-melatonin.aspx?activeingreientid=940 accessed Jan. 5, 2018 in 2 pages.

"Melatonin: in Depth," National Center for Complementary and Integrative Health, accessed May 24, 2018 at https://nccih.nih.gov/health/melatonin in 8 pages.

Bauer, M.D., "Is melatonin a helpful sleep aid—and what should I know about melatonin side effects?" Mayo Clinic, accessed May 24, 2018 at https://www.mayoclinic.org/healthy-lifestyle/adult-health/expert-answers/melatonin-side-effects/faq-20057874 in 7 pages.

Best Naturals Melatonin 10mg 120 Tablets, Amazon, accessed May 24, 2018 at https://www.amazon.com/Best-Naturals-Melatonin-10mg-Tablets/dp/B00K715DIO/ref=sr_1_4_s_it?s=hpc&ie=UTF8&qid=1527188795&sr=1-4&keywords=BEST%2BNATURALS%2BMELATONIN&th=1 in 10 pages.

Reidenberg, "Melatonin and Sleep Disorders," Weill Cornell Medical Center, accessed May 24, 2018 at http://weill.cornell.edu/cert/patients/melatonin.html in 3 pages.

Spring Valley Melatonin Tablets, 1 mg, 120 Ct, Walmart, accessed May 24, 2018 at https://www.walmart.com/ip/Spring-Valley-Melatonin-Tablets-1-mg-120-Ct/15136798?athcpid=15136798&athpgid=athenaItemPage&athcgid=null&athznid=PWVUB&athieid=v0&athstid=CS002&athguid=466001f5-108a112b-d25dedd7445c228a&athena=true in 11 pages.

* cited by examiner

USE OF MELATONIN

The present invention relates to melatonin or a pharmaceutically acceptable salt thereof for use as a medicament, the use of melatonin or a pharmaceutically acceptable salt thereof for the preparation of medicament, the use of melatonin as a food supplement and a pharmaceutical unit dosage form.

Symptoms resulting from alcohol intoxication like hangovers are currently poorly understood from a medical point of view. Health care professionals prefer to study alcohol abuse from a standpoint of treatment and prevention, and there is a view that the hangover provides a useful, natural and intrinsic disincentive to excessive drinking. Not many remedies for the symptoms of alcohol intoxication are known and even trusted literature sources report obscure potentially beneficial remedies like cannabis, food and water, additional alcoholic beverages like Bloody Mary.

Therefore, the objective of the present invention is to provide efficient means to treat alcohol intoxication, related adverse effects of alcohol consumption and in particular to overcome symptoms like hangovers.

The problem of the present invention is solved in a first embodiment by melatonin or a pharmaceutically acceptable salt thereof for use as a medicament in the treatment of acute alcohol intoxication, hangover symptoms or drop in performance after alcohol consumption.

Surprisingly it has been found that melatonin, which is typically used to treat sleeping disorders or ADHD, can be used to treat acute alcohol intoxication and in particular completely eliminate symptoms from alcohol intoxication like hangover symptoms and headaches after consumption of alcoholic beverages. Although the biological mechanism is not yet clearly understood, it is believed that melatonin may increase the rate of conversion of ethyl alcohol to acetaldehyde significantly or—as a highly potent antioxidant—reduces the toxins resulting from the metabolism of ethyl alcohol and simultaneously enhances the natural healing process of the body during physiologic sleep. The natural healing process, detoxification and removal of other symptoms like drop in performance might very well be enhanced by qualitative better physiologic sleep. The blood alcohol level is therefore decreasing at a much higher rate than normal. An alternative or additional mechanism of action could be the scavenging of radicals that build up during the metabolism of the typical ingredients of alcoholic beverages like ethyl alcohol and fusel oils. It is believed that any of these mechanisms may work synergetically and lead to the result.

Since some countries do not allow such claims and since melatonin is considered prescription-only in some countries and a dietary supplement or over-the-counter drug in other countries, the following embodiments reflect this situation:

In a further embodiment, the problem underlying the invention is solved by the use of melatonin or a pharmaceutically acceptable salt thereof for the preparation of a medicament for treating a mammal suffering from acute alcohol intoxication.

In a further embodiment, the problem underlying the invention is solved by use of melatonin as a dietary supplement to avoid hangover symptoms after consumption of alcoholic beverages.

In a further embodiment, the problem underlying the invention is solved by a pharmaceutical unit dosage form comprising an amount of melatonin or a pharmaceutically acceptable salt thereof effective to increase the blood acetaldehyde composition of a mammal in the presence of ethanol following administration thereto and to accelerate the detoxification of alcohol consumption related toxins.

In a further embodiment, the problem underlying the invention is solved by a therapeutic method for treating acute alcohol intoxication comprising administering to an individual afflicted with acute alcohol intoxication an amount of melatonin or a pharmaceutically acceptable salt thereof effective to reduce or eliminate at least one of the symptoms of acute alcohol intoxication and to recover faster.

The following preferred embodiments equally further describe any one of above mentioned embodiments of the invention and are expressly disclosed in any combination, except for the combinations that contradict each other.

Preferably, from 0.1 to 5 mg of melatonin, in particular from 1.5 to 3 mg of melatonin, is administered. This amount of melatonin has been found optimal for elimination symptoms like hangovers or headaches after consumption of ethyl alcohol.

Preferably, the amount of melatonin can be age-adjusted. A higher dosage can be selected for older patients. It is believed that this might help the goal of the invention, because of the fact that physiologic melatonin is decreasing with age.

Preferably, melatonin is administered once before going to sleep. This has been found most useful for avoiding aforementioned symptoms. It has been shown that drinking 0.5 to 2 l of water immediately before or after administration reduced the symptoms further.

Preferably, melatonin is administered via the forms selected from the group inhalation aerosols, sublingual, transdermal, nasal, oral, rectal, intravenous, in particular via the form of a sublingual strip or liquid sublingual administration. It has been found that a sublingual strip or liquid sublingual administration comprising melatonin had the best effect in avoiding aforementioned symptoms compared to the other mentioned forms. It is believed that it may be critical and therefore preferred that the melatonin is quickly released into the blood stream and not digested. Therefore, it is also preferable that melatonin is not in a retard-form and/or not in time released form. Melatonin in retard-form and/or time released form is slowly released over a prolonged period of time. Nowadays, melatonin in retard-form is the common form and to is believed to be working best and most efficiently for all other previously known applications of melatonin. However, in the present invention it was surprisingly found, that melatonin not in retard form worked best to alleviate or eliminate the symptoms after consumption of alcoholic beverages like hangover symptoms or headaches.

EXAMPLE

Subjects were blind to all the experimental treatments.

A person was fed alcoholic beverages containing ethyl alcohol until the blood alcohol concentration reached 310 mg/dL at a time of 10 pm. Next, the person drank 1 l of water and immediately after that was administered a sublingual strip comprising 2.5 mg of melatonin in non-retard form. After that the person went to sleep. After 8 h of physiologic sleep, this person did not suffer from any typical hangover symptoms usually associated with the consumption of alcoholic beverages. This experiment was repeated with 20 other persons with the same effect.

For comparison, the same experiment was conducted with administration of the sublingual strip without melatonin as a placebo. 19 out of 20 persons reported severe typical hangover symptoms like headaches.

The invention claimed is:

1. A method for prevention of headaches arising from alcohol consumption, comprising administering a medicament of melatonin or a pharmaceutically acceptable salt thereof after consumption of alcoholic beverages to a human in need thereof, wherein the melatonin is administered in a pharmaceutical unit dosage form selected from the group consisting of inhalation aerosols, sublingual, transdermal, nasal, oral, rectal, and intravenous, wherein the melatonin prevents the onset of headaches in the human.

2. The method according to claim 1, wherein the melatonin is administered only once before going to sleep.

3. The method according to claim 1, wherein from 0.1 mg to 5 mg of the melatonin is administered.

4. The method according to claim 1, wherein the melatonin is not administered in a retard-form.

5. A method to prevent headaches arising from alcohol consumption, comprising consuming melatonin as a dietary supplement after consumption of alcoholic beverages, the dietary supplement being in the form of an inhalation aerosol, a sublingual strip, or a sublingual liquid, wherein the melatonin prevents the onset of headaches.

6. The method according to claim 5, wherein the dietary supplement is consumed once before going to sleep.

7. The method according to claim 5, wherein from 0.1 mg to 5 mg of the melatonin is consumed.

8. The method according to claim 5, wherein the dietary supplement is consumed as a sublingual strip or a sublingual liquid.

9. The method according to claim 1 wherein from 1.5 mg to 3 mg of the melatonin is administered.

10. The method according to claim 1 wherein the melatonin is administered via the form of a sublingual strip or a sublingual liquid.

11. The method according to claim 5 wherein from 1.5 mg to 3 mg of the melatonin is consumed.

12. A method of preventing headaches arising from consumption of alcoholic beverages, comprising administering a medicament of melatonin or a pharmaceutically acceptable salt thereof after the consumption of alcoholic beverages, the medicament being in the form of an inhalation aerosol, a sublingual strip, or a sublingual liquid, wherein the melatonin is sufficiently effective to prevent the onset of headaches.

13. The method of claim 12, wherein the melatonin is administered in the form of a sublingual strip.

14. The method of claim 1, further comprising drinking 0.5 liters to 2 liters of water before or after administering the medicament of melatonin or a pharmaceutically acceptable salt thereof.

15. The method of claim 5, further comprising drinking 0.5 liters to 2 liters of water before or after consuming the melatonin.

16. The method of claim 12, further comprising drinking 0.5 liters to 2 liters of water before or after administering the medicament of melatonin or a pharmaceutically acceptable salt thereof.

* * * * *